US010538819B2

United States Patent
Nelson

(10) Patent No.: US 10,538,819 B2
(45) Date of Patent: Jan. 21, 2020

(54) COMPOST SYSTEM WITH ERROR DETECTION

(71) Applicant: Whirlpool Corporation, Benton Harbor, MI (US)

(72) Inventor: Keith Nelson, Fort Wayne, IN (US)

(73) Assignee: Whirlpool Corporation, Benton Harbor, MI (US)

( * ) Notice: Subject to any disclaimer, the term of this patent is extended or adjusted under 35 U.S.C. 154(b) by 55 days.

(21) Appl. No.: 15/989,398

(22) Filed: May 25, 2018

(65) Prior Publication Data

US 2018/0274045 A1 Sep. 27, 2018

Related U.S. Application Data

(62) Division of application No. 14/310,045, filed on Jun. 20, 2014, now Pat. No. 10,030,279.

(51) Int. Cl.
| | | |
|---|---|---|
| *C12Q 3/00* | (2006.01) | |
| *C05F 17/00* | (2006.01) | |
| *C05F 17/02* | (2006.01) | |
| *C12M 1/36* | (2006.01) | |

(52) U.S. Cl.
CPC ............ *C12Q 3/00* (2013.01); *C05F 17/0072* (2013.01); *C05F 17/0282* (2013.01); *C12M 41/48* (2013.01); *Y02P 20/145* (2015.11); *Y02W 30/43* (2015.05)

(58) Field of Classification Search
CPC ...... C12Q 3/00; C12M 41/48; C05F 17/0282; C05F 17/0072; Y02P 20/145; Y02W 30/43
See application file for complete search history.

(56) References Cited

U.S. PATENT DOCUMENTS

| | | |
|---|---|---|
| 3,178,267 A | 4/1965 | Larson |
| 5,451,523 A | 9/1995 | Von Fahnestock et al. |
| 5,534,042 A | 7/1996 | Tsuchida |
| 5,559,033 A | 9/1996 | Young |
| 5,591,635 A | 1/1997 | Young et al. |
| 5,890,664 A | 4/1999 | Conant, III |

(Continued)

FOREIGN PATENT DOCUMENTS

| | | |
|---|---|---|
| CN | 201165498 Y | 12/2008 |
| CN | 201569913 U | 9/2010 |

(Continued)

*Primary Examiner* — Shogo Sasaki

(74) *Attorney, Agent, or Firm* — Price Heneveld LLP

(57) ABSTRACT

A controller for a compost system comprises a plurality of control outputs in communication with a plurality of compost devices. The control outputs are configured to identify an error condition of at least one of the plurality of compost devices. The controller is configured to control a first compost device configured to control a first environmental condition and control a second compost device configured to control a second environmental condition of a compost chamber. The controller is further configured to deactivate the first compost device in response to an error condition during a compost cycle. The controller controls the second compost device in response to the first compost device being deactivated preserving the compost cycle by compensating for the error condition in the first compost device.

12 Claims, 5 Drawing Sheets

(56) References Cited

U.S. PATENT DOCUMENTS

| | | | |
|---|---|---|---|
| 5,925,321 A | 7/1999 | Koyamoto et al. | |
| 6,013,177 A | 1/2000 | Hook | |
| 6,352,855 B1* | 3/2002 | Kerouac | C05F 17/0018 435/290.3 |
| 6,383,369 B2 | 5/2002 | Elston | |
| 6,399,366 B1* | 6/2002 | Seagren | C05F 17/0211 241/101.2 |
| 6,627,434 B1 | 9/2003 | McNelly | |
| 7,520,457 B1 | 4/2009 | Poitras et al. | |
| 7,762,713 B2* | 7/2010 | Koh | B01F 7/00208 220/908.2 |
| 7,863,039 B2 | 1/2011 | Campbell et al. | |
| 8,129,177 B2 | 3/2012 | Cohn | |
| 8,304,227 B2 | 11/2012 | Herlihy | |
| 8,361,171 B2 | 1/2013 | Waldron et al. | |
| 8,685,716 B2* | 4/2014 | Bassile | C05F 17/0223 435/290.1 |
| 2007/0175825 A1 | 8/2007 | Denney | |
| 2008/0022739 A1 | 1/2008 | Aswani | |
| 2008/0098779 A1 | 5/2008 | Watson et al. | |
| 2013/0157346 A1 | 6/2013 | Kerouac | |
| 2013/0218493 A1 | 8/2013 | Weddle et al. | |

FOREIGN PATENT DOCUMENTS

| | | |
|---|---|---|
| CN | 202576273 U | 12/2012 |
| CN | 202771228 U | 3/2013 |
| CN | 103102192 A | 5/2013 |
| CN | 103214290 A | 7/2013 |
| CN | 103309291 A | 9/2013 |
| EP | 0606617 B1 | 7/1997 |
| KR | 20030073954 A | 9/2003 |
| WO | 2009095713 A1 | 8/2009 |

\* cited by examiner

COMPOST SYSTEM WITH ERROR DETECTION

CROSS-REFERENCE TO RELATED APPLICATIONS

This application is a divisional of U.S. patent application Ser. No. 14/310,045, entitled "COMPOST SYSTEM WITH ERROR DETECTION," filed on Jun. 20, 2014, now U.S. Pat. No. 10,030,279. The entire disclosure of the application is hereby incorporated by reference.

BACKGROUND

The present disclosure relates generally to a compost system and more particularly relates to a controller for a compost system.

SUMMARY

In one aspect of the present disclosure a controller for a compost system is disclosed. The controller comprises a plurality of control outputs in communication with a plurality of compost devices. The control outputs are configured to identify an error condition of at least one of the plurality of compost devices. The controller is configured to control a first compost device of the plurality of compost devices configured to control a first environmental condition of a compost chamber and control a second compost device of the plurality of compost devices configured to control a second environmental condition of the compost chamber. The controller is further configured to identify the error condition of the first compost device and deactivate the first compost device in response to the error condition during a compost cycle. The controller controls the second compost device in response to the first compost device being deactivated preserving the compost cycle by compensating for the error condition in the first compost device.

In another aspect of the present disclosure, a method for controlling a compost system is disclosed. The method comprises selectively actuating a first compost device of the compost system. The first compost device is configured to control a first environmental condition of a compost chamber. The method further comprises selectively actuating a second compost device of the compost system. The second compost device is configured to control a second environmental condition of the compost chamber. The method further comprises monitoring the operation of the first compost device and detecting an error condition in the first compost device. In response to the error condition, the operation of the first compost device is limited. In response to the limited operation of the first compost device, the second compost device is controlled preserving the compost cycle by compensating for the error condition in the first compost device.

These and other features, advantages, and objects of the present device will be further understood and appreciated by those skilled in the art upon studying the following specification, claims, and appended drawings.

DETAILED DESCRIPTION OF EMBODIMENTS

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more implementations. In one or more instances, well-known structures and components are shown in block diagram form in order to avoid obscuring the concepts of the subject technology.

Figure 1:
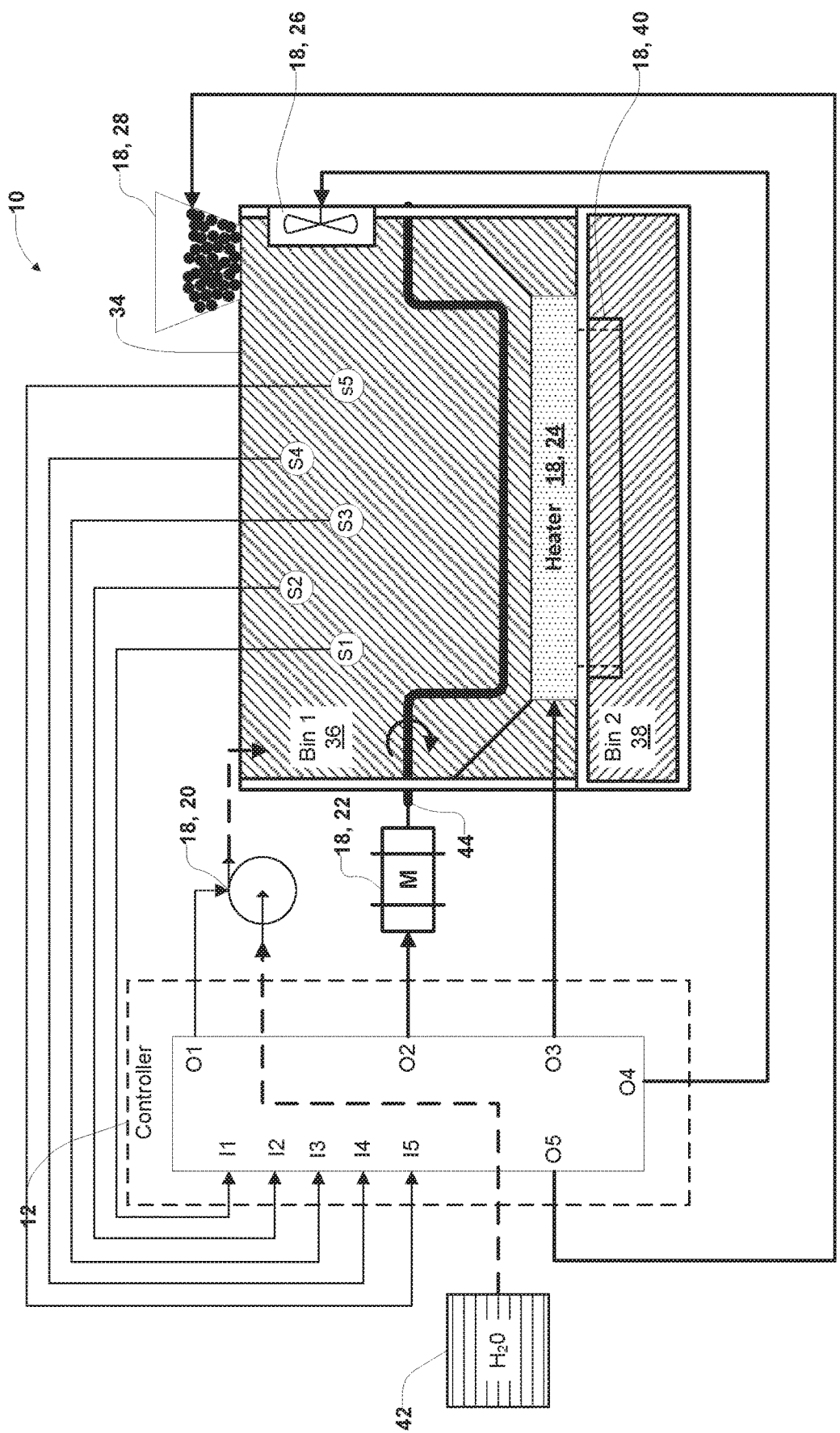
FIG. 1 is a block diagram of a compost system utilizing a controller configured to identify and control errors in the compost system.
Figure 2:
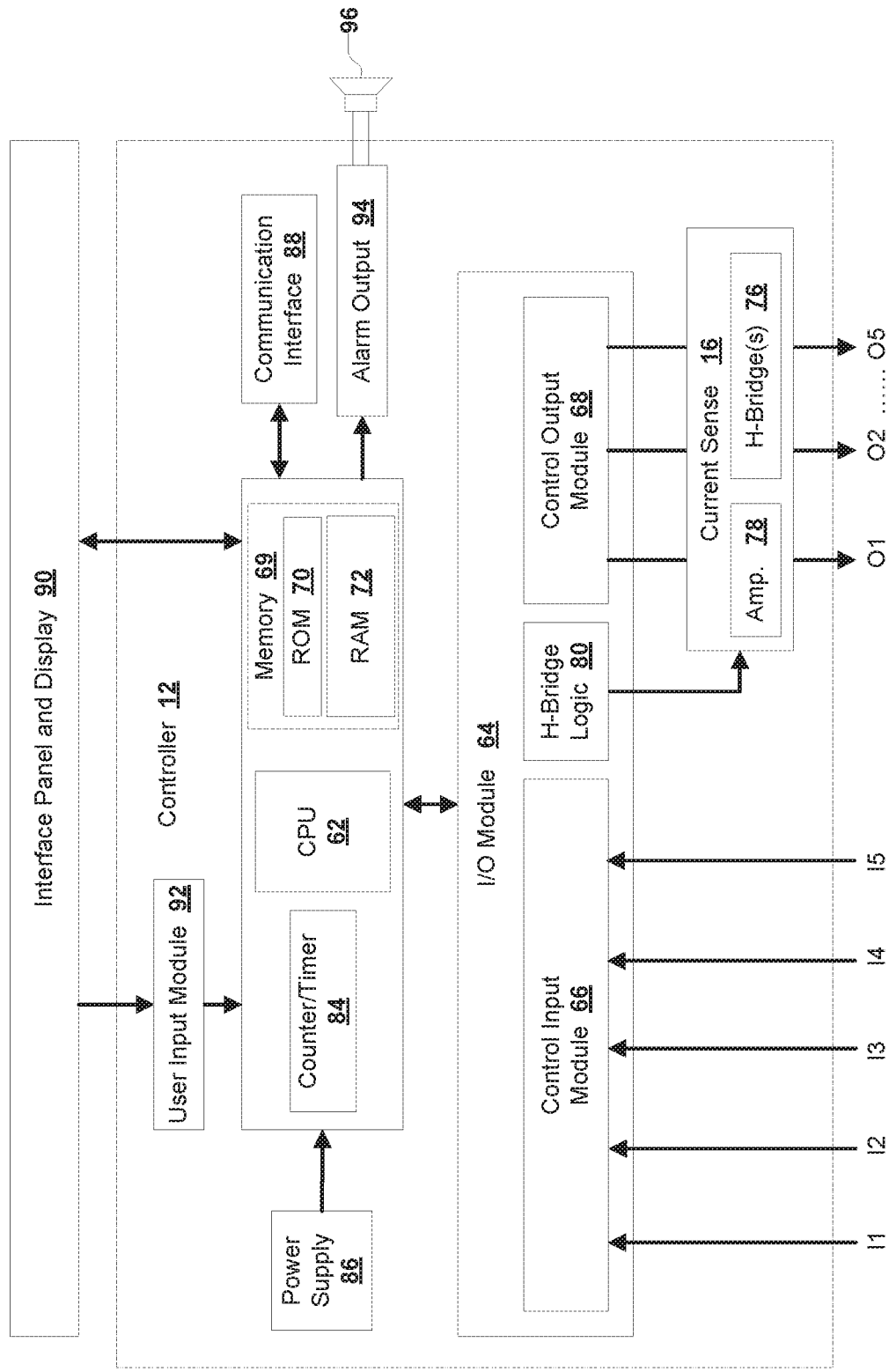
FIG. 2 is a block diagram of a controller configured to identify and control errors in a compost system.

Referring to FIGS. 1 and 2, a compost system 10 is shown demonstrating a controller 12 configured to identify and control errors in the compost system 10. The controller 12 comprises at least one control output, for example, one of a plurality of control outputs O1, O2, O3, O4, and O5. The controller 12 comprises one or more circuits (e.g. load sensing circuits) configured to monitor the load current conditions for each of the control outputs O1-O5. A load current of each of the control outputs O1-O5 may be monitored by the controller 12 to determine abnormal load current conditions for each of the control outputs O1-O5.

The at least one control output is in communication with a compost device 18. The compost device 18 may correspond to any device configured to control an operation, a process, and/or an environmental condition of the compost system 10. In some implementations, the compost device 18 may comprise a water supply device 20, a tiller motor 22, a heater 24, a fan 26, a feeder 28, a bin transfer device, and various devices that may be utilized in, or implemented in combination with, the compost system 10. The compost device 18 is configured to control an environmental condition of a compost chamber 34 of the compost system 10.

The controller 12 is operable to monitor the load sensing circuits and generate a load value to quantify the load current. With the load value, the controller 12 is operable to compare the load value to at least one predetermined value or current threshold value to determine an error condition of the compost system 10. The various methods and systems disclosed herein provide for enhanced operation of compost systems by identifying and controlling error conditions to prevent damage to the compost system 10 and the compost devices 18.

In some embodiments, the controller 12 is operable to maintain an operation of one or more compost devices even after an error condition has been identified by the controller 12. An error condition may comprise any state of operation of at least one composting device outside of normal operating parameters. For example, an error condition may include a blockage, a breakage, a malfunction, an over or under-current condition, an overheating condition, or any other condition outside of normal operation of the compost devices 18. By maintaining safe operation of the compost system 10 and the compost devices 18 after an error condition has been detected, this disclosure provides for systems and methods operable to continue production of compost, even after one or more input devices is identified as malfunctioning.

Referring again to FIG. 1, the compost chamber 34 includes a first bin 36 and a second bin 38. During processing of biodegradable refuse, refuse materials, or compost materials, the compost system 10 utilizes the first bin 36 to process and condition the refuse to ensure that the refuse materials are efficiently decomposed to generate compost. Processing and conditioning the refuse material may include adding water, controlling airflow, tilling, heating, adding coir pellets, and any other processes that may be utilized in a composting system. The controller 12 is operable to control the environmental conditions within the first bin 36 during various stages of decomposition of the refuse based on one or more settings and/or algorithms programmed in a memory of the controller 12. Once the refuse materials are decomposed and compost is formed, the controller 12 is operable to open a transfer door 40 to transfer the compost from the first bin 36 to the second bin 38.

The controller 12 is configured to monitor the refuse material in the first bin 36 via a plurality of signal inputs I1-I5. The signal inputs I1-I5 may comprise various forms of inputs configured to receive signals from one or more sensors or transducers. In some embodiments, the signal inputs I1-I5 may be implemented as digital inputs or analog inputs in communication with at least one analog to digital (A/D) converter that may be incorporated in the controller 12. Each of the plurality of signal inputs I1-I5 is in communication with a transducer S1-S5 configured to monitor an environmental condition of the compost chamber 34.

In an exemplary embodiment, the first signal input I1 is in communication with a first transducer S1, the second signal input I2 is in communication with a second transducer S2, and the third signal input I3 is in communication with a third transducer S3. Each of the signal inputs I1-I5 is configured to receive signals corresponding to the environmental conditions of the compost chamber 34 from the transducers S1-S5. Though the implementation demonstrated in FIG. 1 illustrates five signal inputs I1-I5 corresponding to five transducers S1-S5, the controller 12 may be configured to incorporate any number of signal inputs corresponding to any number of transducers utilized in a particular compost system.

The transducers S1-S5 may be configured to monitor a variety of environmental conditions corresponding to the compost chamber 34. For example, environmental conditions may include a humidity level, an oxygen level, and a temperature within the compost chamber 34, as well as any other environmental condition that may be monitored in the compost system 10. In an exemplary implementation, the first transducer S1 is an oxygen sensor, the second transducer S2 is a humidity sensor, and the third transducer S3 is a temperature sensor. Each of the transducers S1-S5 discussed herein may be implemented by a variety of sensors. For example, the oxygen sensor may be a zirconia oxygen sensor, the humidity sensor may be a resistive or capacitive humidity sensor, and the temperature sensor may be a resistive or infrared temperature sensor. Though particular transducers are described herein, a variety of sensor types may be utilized without departing from the spirit of the disclosure.

In response to the environmental conditions determined from the signals received by the signal inputs I1-I5, the controller 12 may adjust the environmental conditions of the compost chamber 34 by controlling a plurality of compost devices 18. Each of the control outputs O1-O5 is configured to control a compost device 18. The control outputs O1-O5 are configured as follows:

the first control output O1 is configured to control the water supply device 20;

the second control output O2 is configured to control the tiller motor 22;

the third control output O3 is configured to control the heater 24;

the fourth control output O4 is configured to control the fan 26; and the fifth control output O5 is configured to control the feeder 28.

Though the implementation demonstrated in FIG. 1 illustrates five control outputs O1-O5 corresponding to five compost devices 18, the controller 12 may be configured to incorporate any number of control outputs corresponding to compost devices utilized in a particular compost system.

The water supply device 20 may be implemented as a water pump or a water control valve configured to control water supplied to the compost chamber 34 from a water supply 42. The water supply device 20, as well as the tiller motor 22, the fan 26, and the feeder 28, may utilize electric motors. The electric motors may be of any form, and in some implementations may be stepper motors, servomotors, alternating current (AC) motors and/or direct current (DC) motors. Depending on a particular electric motor implemented for each of the compost devices 20, 22, 24, 26, 28, the corresponding output controls O1, O2, O3, O4, and O5 may be configured to control the particular electric motor corresponding to a particular compost device 18.

The tiller motor 22 is coupled to a tiller bar 44 and is operable to rotate the tiller bar 44 to aerate the refuse material in the first bin 36 of the compost chamber 34. The heater 24 is positioned within the compost chamber 34 and operable to supply heat to the refuse material. The heater 24 may comprise electrically resistive elements configured to heat the refuse material in response to current supplied by the controller 12. The fan 26 is in fluid communication with an oxygenated air source and is configured to move compost odors through a filter system and supply air into the compost chamber 34. The feeder 28 is operable to supply composting of coir pellets into the compost chamber 34 by actuating an agitator to selectively feed a desired number of coir pellets into the compost chamber 34. Via the control outputs O1-O5, the controller 12 is operable to selectively activate and deactivate each of the compost devices 18 to adjust the environmental conditions within the compost chamber 34.

In an exemplary embodiment, the controller 12 is configured to monitor the load current drawn by each of the compost devices 18 including the load current drawn by the water supply device 20, the load current drawn by the tiller motor 22, the load current drawn by the heater 24, the load current drawn by the fan 26, and the load current drawn by the feeder 28. During operation of each of the compost devices 18, the controller 12 is configured to measure at least one current drawn by the compost devices 18 and generate a load value. The load value is compared by the controller 12 to a first current threshold and a second current threshold to ensure that each of the compost devices 18 is operating properly.

Each of the compost devices 18 may have different operating parameters expected during normal operation. Accordingly, based on the operating parameters of each of the compost devices 18, a first current threshold and a second current threshold may be stored in a memory of the controller 12. The first and second current thresholds may correspond to predetermined values corresponding to normal and safe operating parameters of each of the compost devices 18. The controller 12 is configured to store a specific first current threshold and a specific second current threshold corresponding to each of the compost devices 18 for comparison to load values measured by the controller 12 to detect an error condition.

The first current threshold may correspond to a minimum normal operating current and the second current threshold may correspond to a maximum normal operating current corresponding to each of the compost devices 18. The controller 12 is configured to store the current thresholds for each of the compost devices 18 as load current profiles. The load current profile for a specific compost device (e.g. the heater 24) may be accessed by the controller 12 to compare the current load of the compost device to the normal operating parameters. In this way, the controller is operable to detect an error condition for each of the compost devices 18 while controlling the compost system 10.

The following example illustrates a detection of an error condition identified by the controller 12. In response to the first transducer S1 (e.g., the oxygen sensor) communicating to the controller that the oxygen level in the compost chamber 34 is below a desired level, the controller 12 is configured to activate one or more of the control outputs O1-O5 to increase the oxygen level. The controller 12 may activate the fan 26 via the fourth control output O4 and the tiller motor 22 via the second control output O2. During operation of the fan 26 and the tiller motor 22, the controller 12 may monitor the load current drawn by the fourth output O4 corresponding to the fan 26 and the second output O2 corresponding to the tiller motor 22. By monitoring the current of the active compost devices 18, the controller 12 is configured to determine the electrical current or load current drawn by the fan 26 and the tiller motor 22.

The controller 12 is further operable to generate a load value to quantify each of the load currents measured from the fourth output O4 and the second output O2. If the load value determined for the fourth output O4 is less than a first fan current threshold or greater than a second fan current threshold based as determined from the current profile for the fan 26, the controller 12 is configured to identify an error condition for the fan 26. If the load value is less than the first fan current threshold, the controller 12 is operable to determine that the fan 26 is in a non-operational condition. For example, the fan motor may be damaged such that there is a smaller load current draw than is required for operation of the fan 26. If the load value is greater than the second fan current threshold, the controller 12 is operable to determine that the fan motor is operating in an over-current condition. The over-current condition may correspond to a fan blade blocked by foreign material, an overheating condition that may correspond to inefficient operation, or a variety of additional error states for the fan motor, and consequently, the fan 26. In response to the controller 12 identifying an error condition for the fan 26, the controller 12 is configured to de-activate or limit the fourth control output O4.

Though the first threshold level and the second threshold level are discussed in reference to the fan 26, each of the compost devices 18 is similarly configured to have a first threshold level and a second threshold level corresponding to an operation or current profile. Each of the current profiles corresponds to predetermined values or expected load current values that define normal operating parameters of each of the compost devices 18 (e.g., the water supply device 20, the tiller motor 22, the heater 24, the feeder 28, and any other input devices incorporated in the compost system 10). In response to the load current being less than the first threshold level or greater than the second threshold level, the controller 12 is configured to report an error condition. The error condition corresponds to a particular compost device having a current load draw below or above the first and second threshold levels.

In response to the error condition, the controller 12 is further configured to deactivate the corresponding compost device by deactivating the control output in communication with the corresponding compost device. For example, in response the controller 12 identifying the load current drawn by the tiller motor 22 exceeds a second current threshold level, the controller 12 is configured to deactivate the second control output O2. By monitoring the load current drawn by each of the compost devices 18, the controller 12 is operable to ensure proper operation of the compost devices 18.

In some embodiments, controller 12 is further operable to continue to monitor and control the compost devices 18 even after one or more of the compost devices 18 is determined to be in an error condition. For example, if a water pump motor of the water supply device 20 is identified by the controller 12 as being in an error condition, the controller 12 is configured to utilize the remaining compost devices 18 to attempt to maintain a plurality of desired environmental conditions of the compost chamber 34. By attempting to maintain the desired environmental conditions, the controller 12 is operable to prevent a compost batch from loss that may occur if all of the compost devices 18 are deactivated. Further details of various methods of control and systems of the compost system 10 are provided in reference to FIGS. 2-5.

Referring again to FIG. 2 a block diagram of the controller 12 is shown. The controller 12 ensures proper compost production by measuring and adjusting the conditions of the refuse material over time. For example, the conditions of the compost may change over time due to the decomposition of refuse materials added to the compost chamber 34. These environmental conditions in the compost chamber 34 are tracked by a processing unit 62 via the signal inputs I1-I5. By monitoring the environmental conditions in the compost chamber 34, the controller 12 is operable to monitor and regulate the environmental conditions for the compost during various stages of decomposition to ensure that the compost is efficiently generated.

Each of the signal inputs I1-I5 and the control outputs O1-O5 are in communication with the controller 12 via an input output (I/O) module 64. The signal inputs I1-I5 may comprise analog or digital inputs of a control input module 66 of the I/O module 64. The control outputs O1-O5 are output by a control output module 68 of the I/O module 64. In operation, the controller 12 is operable to monitor and control the environmental conditions of the compost chamber 34 via the control input module 66 and the control output module 68.

The controller 12 utilizes the processing unit 62 to determine the environmental conditions in the compost chamber 34 measured by the transducers S1-S5 via signals received by the signal inputs I1-I5. The controller 12 is configured to adjust the environmental conditions by controlling the compost devices 18 via the control outputs O1-O5. The controller 12 comprises one or more processing modules stored in a suitable memory device 69, which may include a read only memory (ROM) 70 and a random access memory (RAM) 72. The one or more processing modules are operable to determine a desired environmental condition for the refuse material according to various stages of decomposition based on data received from the transducers S1-S5. The processing unit 62 may access the ROM 70 and/or the RAM 72 to determine a control scheme for the environment of the compost chamber 34 comprising a timing of an operation (e.g., timing to activate the tiller motor 22) and/or a quantity of materials (e.g., water, coir pellets) to add to the compost chamber 34 based on the processing modules. The processing modules of the controller 12 may comprise one or more algorithms, tables, and/or logical controls configured to monitor and control the maturation of the compost over time.

As discussed herein, the controller 12 is operable to detect an error state of at least one of the compost devices 18 via one or current sensing circuits. In some embodiments, a current sensing device 16 may comprise a shunt resistor measuring the current load drawn by each of the compost devices 18. The voltage $V_{sense}$ measured across the shunt resistor is may be measured by the controller 12 to determine the load current and generate the load current value corresponding to each of the outputs O1-O5.

The controller may utilize at least one H-bridge circuit 76 to control a direction of a DC motor, for example the tiller motor 22. The H-bridge circuit 76 is controlled by the controller via an H-bridge logic control output 80 of the I/O module 64. The H-bridge logic control output 80 is configured to control a switching configuration of the H-bridge circuit 76 to control a path of electrical current therethrough and consequently control a direction of a DC motor.

The processing unit 62 receives power from a power supply 86 and also comprises a communication interface 88 operable to provide access for service and/or access to an external storage device and/or any form of machine readable media. The compost system 10 includes an interface panel and display 90 configured to present information to an operator of the compost system 10. The interface panel and display 90 is also configured to receive inputs to program various operations of the controller 12 from a plurality of switches. Each of the plurality of switches is in communication with a user input module 92 configured to communicate a user selection to the controller 12 from the plurality of switches.

The interface panel and display 90 is configured to provide a user interface for an operator of the compost system 10 to configure the controller 12 for a particular operation and communicate graphical information to the operator. The controller 12 further comprises an alarm output 94 configured to signal an error state identified in each of the compost devices 18. The alarm output 94 is in communication with a speaker 96 configured to audibly alert the operator of an error condition.

Figure 3:
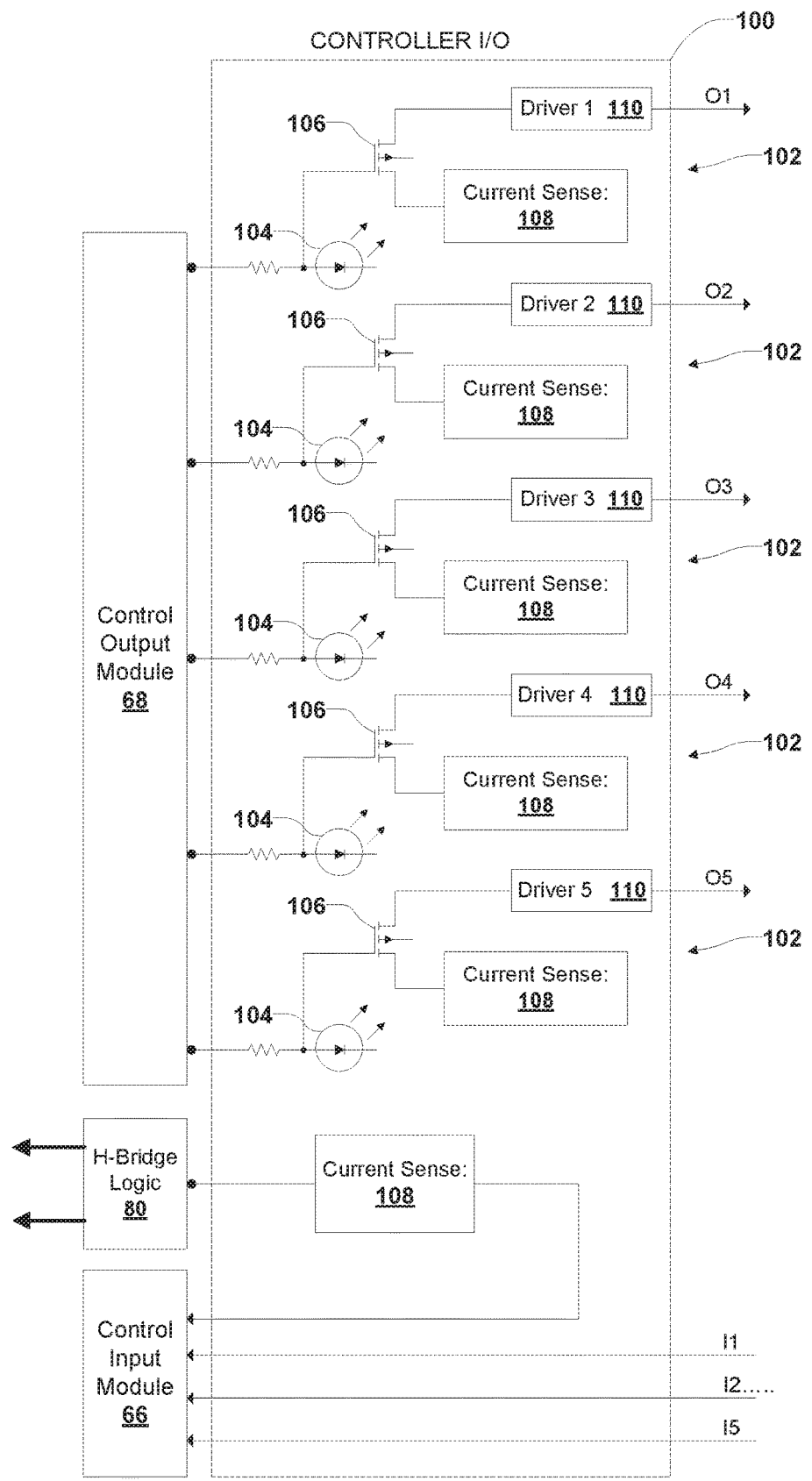
FIG. 3 is a schematic diagram of a control circuit configured to selectively activate a current sensing function.

Referring to FIG. 3, a schematic diagram of a control circuit 100 configured to selectively activate a current sensing function is shown. As discussed herein, the control output logic 68 is configured by the H-bridge logic control output 80 to provide directional control for DC devices. The controller 12 is configured to measure the current draw from each of the control outputs O1-O5. Each of the control outputs O1-O5 comprises an output circuit 102. In response to the controller 12 activating each of the control outputs O1-O5, the controller measures the current draw of each of the outputs O1-O5 and generates a current level or load value. The current level or load value may comprise an analog or digital value or signal that may be utilized by the controller 12 to determine if the current draw is within a normal operating range.

In addition a light source 104, for example, a light emitting diode (LED), is activated on the interface panel and display 90. Each light source 104 is configured to notify the operator of an active compost device 18. Additionally, in response to an active control output O1-O5, a transistor 106 is configured to detect an abnormal current condition by selectively providing for current sensing for each of the outputs O1-O5. The load current for the active compost device 18 is then monitored by the controller 12 via the control input module 66 to determine if an abnormal current draw is detected from the a compost device 18 resulting in a system error condition.

Each of the control outputs O1-O5 may further comprise a driver 110. Each of the drivers 110 is configured to control a compost device 18 corresponding to each of the control outputs O1-O5. The drivers 110 may be configured having different parameters, functions, and architecture corresponding to a particular compost device 18 (e.g., the tiller motor 22, the heater 24, etc.).

The signal inputs I1-I5 are also shown in FIG. 3 demonstrating a schematic view of the system inputs in communication with the controller 12 via the control input module 66. Based on the signal inputs and corresponding signals received from the transducers (S1-S5), the controller 12 is configured to selectively activate each of the control outputs O1-O5 to control each of the compost devices 18. In this configuration, the controller 12 is operable to selectively monitor the current load drawn by each of the compost devices 18 to ensure that the compost system 10 operates safely and effectively.

Figure 4:
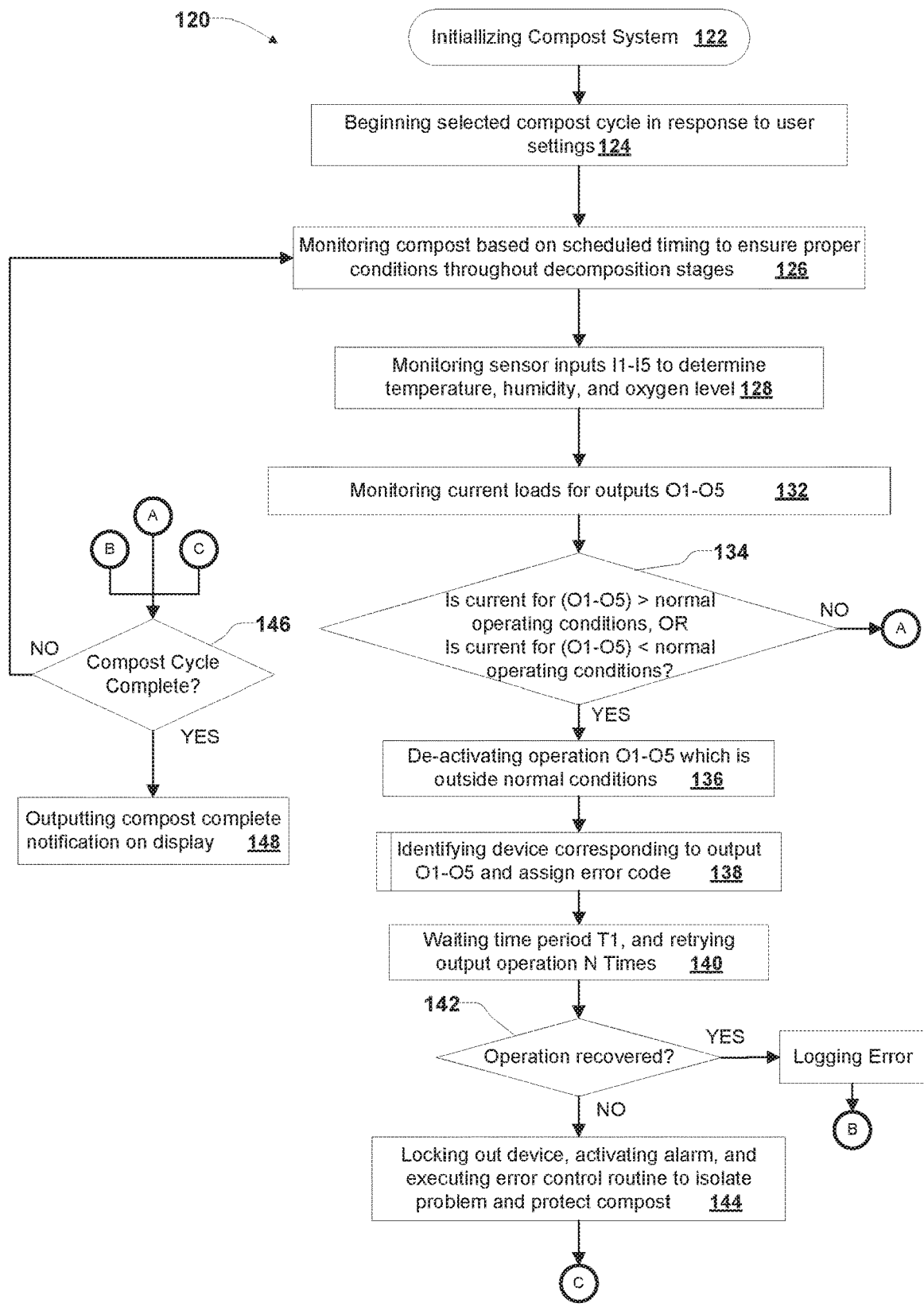
FIG. 4 is a flow chart demonstrating a method for controlling a compost system.

Referring to FIG. 4, a flow chart demonstrating a method 120 for controlling the compost system 10 is shown. The method 120 begins by the controller 12 initializing the compost system 10 to begin a composting cycle (122). The controller 12 may begin the composting cycle corresponding to user settings received from an operator of the compost system 10 via the interface panel and display 90 (124). During the composting cycle, the controller 12 monitors the compost based on scheduled timing to ensure that refuse material in the compost chamber 34 achieves the proper conditions throughout the various decomposition stages of the refuse material (126).

The controller 12 is further operable to monitor the signal inputs I1-I5 to determine the temperature, humidity level, and an oxygen level of the compost chamber 34 (128). Based on the signal inputs I1-I5, the controller 12 selectively outputs control signals via the control outputs O1-O5 to regulate the environmental conditions of the compost chamber 34 (130). In response to an active state of any of the control outputs O1-O5, the controller 12 is configured to monitor the load current drawn by an active compost device 18 (132). While monitoring the load current drawn by an active compost device 18, the controller 12 may determine if the active compost device 18 is drawing current outside of the normal operating conditions for the particular compost device 18 (134).

As discussed herein, the normal operating conditions for a particular compost device 18 correspond to the first threshold level and the second threshold level. Each of the threshold levels correspond to predetermined values or an expected range of load current values that define normal operating parameters of each of the compost devices 18 (e.g., the water supply device 20, the tiller motor 22, the heater 24, the feeder 28, and any other input devices incorporated in the compost system 10). In response to the controller 12 determining that the load current for the active compost device 18 being within the normal operating parameters (e.g., above a first threshold level and below a second threshold level), the controller 12 is configured to continue the compost cycle by progressing to a reference step A.

In response to the load current for the active compost device 18 being less than the first threshold level or greater than the second threshold level, the controller 12 is configured to deactivate the active compost device 18 by deactivating the corresponding output control O1-O5 (136). Hereinafter, the deactivated compost device 18 and corresponding deactivated output control O1-O5 are referred to as the malfunctioning compost device and the deactivated output control, respectively. The controller 12 then continues to identify the compost device 18 corresponding to the deactivated output control of step 136 and assign an error code in the memory device 69 (138). The error code may identify the malfunctioning compost device for later service or repair.

Following the identification of an error condition, the controller 12 may enter a recovery routine by waiting for a time period T1 and retrying an output operation (140). The controller 12 may retry the output operation, depending on load conditions detected by the controller 12, N times by reactivating the malfunctioning compost device via the previously deactivated output control and monitoring the load current of the malfunctioning compost device as in step 134. The time period T1 and the number of recovery attempts N as discussed herein may be any number or value. In an exemplary implementation, the time T1 is approximately 2 minutes and the number of recovery attempts N is 4.

By retrying the output operation, the controller 12 determines if the malfunctioning compost device has recovered from an error condition (142). If the malfunctioning compost device is determined to have recovered (e.g., the current draw is within normal operating parameters), the controller 12 is configured to log an error code identifying the malfunctioning compost device in the memory device 69 and proceed to a reference step B. If the malfunctioning compost device is determined not to have recovered (e.g., the current draw is outside normal operating parameters), the controller 12 locks out the malfunctioning compost device and activates the alarm output 94 (144). Following step 144, the controller 12 is configured to progress to a reference step C, such that the controller 12 may determine if the compost cycle has completed the recovery routine. In response to the malfunctioning compost device being unable to recover from the error condition, the controller 12 is further operable to execute an error control routine to isolate the error and protect the composting process. The error control routine is further discussed in greater detail in reference to FIG. 5.

Following each of reference steps A, B, and C, the controller 12 determines if the compost cycle is complete (146). If the compost cycle is complete, the controller 12 is configured to move the refuse material from the first bin 36 to the second bin 38 and output a notification that the compost is complete on the interface panel and display 90 (148). If the compost cycle is not complete, the controller 12 continues to step 126 to monitor the refuse material throughout the decomposition stages of compost production. The method 120 provides for safe operation of the compost system 10 by monitoring the compost device 18 and alerting an operator in the event of an error condition. The systems and methods described herein provide various benefits that may prevent damage to the compost system 10 and ensure safe operation.

Figure 5:
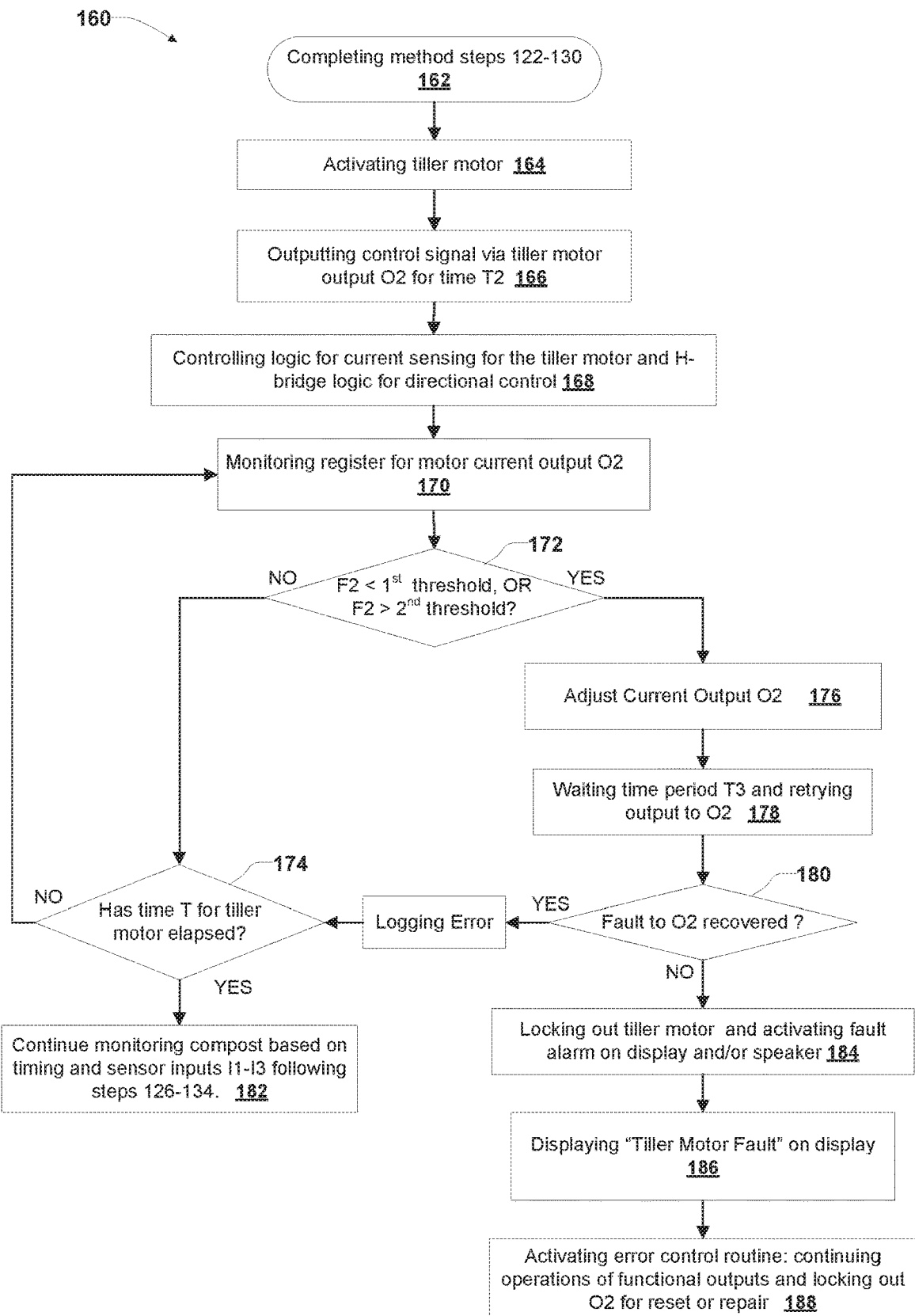
FIG. 5 is a flow chart demonstrating a method for controlling a compost system in accordance with the disclosure.

Referring to FIG. 5, a flow chart demonstrating a method 160 for controlling the compost system 10 is shown. The method 160 begins by completing method steps 122 through 130 of the method 120 and is discussed to provide an exemplary operation of the controller 12 in reference to the tiller motor 22 (162). Based on the scheduled timing of the composting cycle and/or the environmental conditions determined by the signal inputs I1-I5, the controller 12 activates the tiller motor 22 to churn and aerate the refuse material in the first bin 36 with the tiller bar 44 (164). To activate the tiller motor 22, the controller 12 outputs a control signal via the second output O2 for a time T2 (166). The controller 12 may then control the H-bridge logic 80 for the directional control of the tiller motor 22 and measure the current draw from control output O2 (168). Any two outputs (O1-O5) can be configured via the controller 12, as an H-bridge logic circuit driver 80 to change voltage polarity for DC devices that require directional operation, such as the tiller motor 22.

The controller 12 is operable to measure the current supplied by the outputs (O1-O5) via a current measuring capability and can be configured to detect when a particular output O1-O5 exceeds or falls below a current threshold range. The controller is configured to monitor a register for the load value corresponding to the current output O2 (170). The controller can then analyze the situation by determining if the load value for O2 is above or below a current threshold range (172). If one of the load values for the outputs O1-O5 is determined to be within the current threshold range for the particular output O1-O5, the controller 12 may determine that the compost devices are functioning properly and continues to determine if the time T2 for the device has elapsed (174). If the value from outputs O1-O5 is determined to be out of range from the current threshold range for the output O1-O5, the controller 12 is configured to identify an error condition and deactivate or limit operation of the device, logging a system error (176).

In response to the error condition, the controller 12 enters a recovery routine by waiting for a time period T3 and retrying the output operation via the second control output O2 (178). The controller 12 may retry the output operation N times by reactivating the tiller motor 22 via the second control output O2 and monitoring the load current. The time periods T2 and T3 as discussed herein may be any time period. In an exemplary implementation, the time T2 may vary based on a particular composting system and the environmental conditions detected in the compost chamber 34. The time T3 may also vary and is approximately 2 minutes in some implementations.

By retrying the output operation, the controller 12 determines if the malfunctioning tiller motor 22 has recovered from the error condition (180). If the tiller motor 22 is determined to have recovered (e.g., the current draw is within normal operating parameters), the controller 12 is configured to log an error code corresponding to the error identified for the tiller motor 22 in the memory device 69 and proceed to step 174. In step 174, if the time T for the tiller motor 22 to be activated has elapsed, the controller 12 continues to monitor the compost system 10 similar to steps 126-134 of the method 120 (182).

In step 180, if the tiller motor 22 is determined not to have recovered (e.g., the current load is outside normal operating parameters), the controller 12 locks out or limits the tiller motor 22 via the second control output O2 and activates the alarm output 94 (184). The controller 12 also displays an error notification on the interface panel and display 90 describing the error condition of the compost system 10 (186). For example, the controller 12 may display "Tiller Motor Fault" describing the error identified in the tiller motor 22. In response to the malfunctioning compost device being unable to recover from the error condition, the controller 12 is further operable to execute an error control routine to isolate the error and protect the composting process.

The error control routine, as discussed herein, provides for various steps that allow the controller 12 to continue a composting cycle after a malfunctioning compost device has been identified and the controller 12 has taken the appropriate action to isolate or limit the device operation. As an example, an error control routine is now described in reference to the method 160. Following a locking out or limiting operation of the tiller motor 22 and the corresponding second control output O2, operation of other compost devices 18 may continue to attempt to preserve the compost cycle. By controlling a plurality of operational compost devices 18 while at least one of the compost devices 18 is in an error condition, the controller 12 is operable to preserve the composting cycle.

The controller 12 is operable to preserve a composting cycle by monitoring the signal inputs I1-I5 and controlling the plurality of operational compost devices 18 to provide proper conditions for the decomposition of refuse material. By monitoring the signal inputs I1-I5, the controller 12 may determine that the fan 26 should be activated for a longer period of time than in conditions when the tiller motor 22 is operational. Similarly, the controller 12 may determine that water supplied to the compost chamber 34 should be limited due to the error condition of the tiller motor 22. By changing the response of the controller 12 to the environmental conditions identified by the transducers S1-S5 based on at least one malfunctioning compost device, the controller 12 is operable to preserve a composting cycle and prevent the loss of the compost being processed in a compost cycle.

The term "computer-readable medium" as used herein refers to any medium that participates in providing instructions to the processing unit 62 for execution. Such a medium may take many forms, including, but not limited to, non-volatile media, volatile media, and transmission media. Non-volatile media include, for example, optical or magnetic disks. Volatile media include dynamic memory, such as the RAM 72. Common forms of computer-readable media include, for example, a floppy disk, a flexible disk, a hard disk, a magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and an EPROM, a FLASH-EPROM, any other memory chip or cartridge, a carrier wave, or any other medium from which a computer can read.

Various forms of computer-readable media may be involved in providing instructions to the processing unit 62 for execution. For example, the instructions for carrying out at least part of the present disclosure may be accessed from the ROM 70, the RAM 72, and the communication interface 88, which may further be in communication with a storage device. The processing unit 62 is configured to retrieve and execute the instructions based on data received from the control input module 66, the communication interface 88, the memory device 69, and various devices that may be in communication with the controller 12. The instructions received by the RAM 72 can optionally be stored on a storage device either before or after execution by a processor.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above is merely for illustrative purposes and not intended to limit the scope of the device, which is defined by the following claims.

What is claimed is:

1. A controller for a compost system having a plurality of compost devices, the controller comprising:
   a plurality of control outputs in communication with the plurality of compost devices, wherein the control outputs are configured to identify an error condition of at least one of the plurality of compost devices, wherein the controller is configured to:
   control a first compost device of the plurality of compost devices configured to control a first environmental condition by controlling a tiller configured to mix a material in a compost chamber;
   control a second compost device of the plurality of compost devices configured to control a second environmental condition by controlling a fan configured to circulate air in the compost chamber;
   identify the error condition of the first compost device;
   deactivate the first compost device in response to the error condition during a compost cycle; and
   control the second compost device in response to the first compost device being deactivated, wherein the second compost device is controlled thereby preserving the compost cycle by compensating for the error condition in the first compost device.

2. The controller according to claim 1, wherein the plurality of compost devices comprise at least one of a water pump, an electric motor, and a heater.

3. The controller according to claim 1, wherein the controller further comprises:
   a measurement circuit operable to selectively measure a load current of each of the plurality of control outputs.

4. The controller according to claim 1, further comprising:
   a plurality of signal inputs configured to receive signals identifying the environmental conditions of the compost chamber.

5. The controller according to claim 4, wherein the environmental conditions comprise one or more of an oxygen level, a temperature, and a humidity level in the compost chamber.

6. The controller according to claim 1, wherein the controller is further configured to:
   control the second output adjusting an operation time of the fan thereby preserving the compost cycle in response to the deactivation of the first compost device.

7. A method for controlling a compost system having a plurality of compost devices, the method comprising:
   selectively actuating a first compost device of the compost system, wherein the first compost device is configured to control a first environmental condition by controlling a tiller configured to mix a material in a compost chamber;

selectively actuating a second compost device of the compost system, wherein the second compost device is configured to control a second environmental condition by controlling a fan configured to circulate air in the compost chamber;
monitoring the operation of the first compost device;
detecting an error condition in the first compost device;
limiting operation of the first compost device in response to the error condition; and
controlling the second compost device in response to the limited operation of the first compost device, wherein the second compost device is controlled thereby preserving the compost cycle by compensating for the error condition in the first compost device.

8. The method according to claim 7, further comprising:
selectively measuring the load current of each of the plurality of compost devices to identify the error condition.

9. The method according to claim 7, further comprising:
receiving at least one signal from a transducer configured to detect at least one of the environmental conditions of the compost chamber.

10. The method according to claim 9, wherein the environmental conditions comprise at least one of an oxygen level, a temperature, and a humidity level in the compost chamber.

11. The method according to claim 7, wherein controlling the second compost device in response to the limited operation of the first compost device comprises adjusting an operation time of the second compost in response to the limited operation of the first compost device.

12. The method according to claim 11, wherein adjusting the operation time of the second compost device comprises increasing an operating time of the fan preserving the compost cycle in response to the limited operation of the first compost device.

* * * * *